Figure 1:
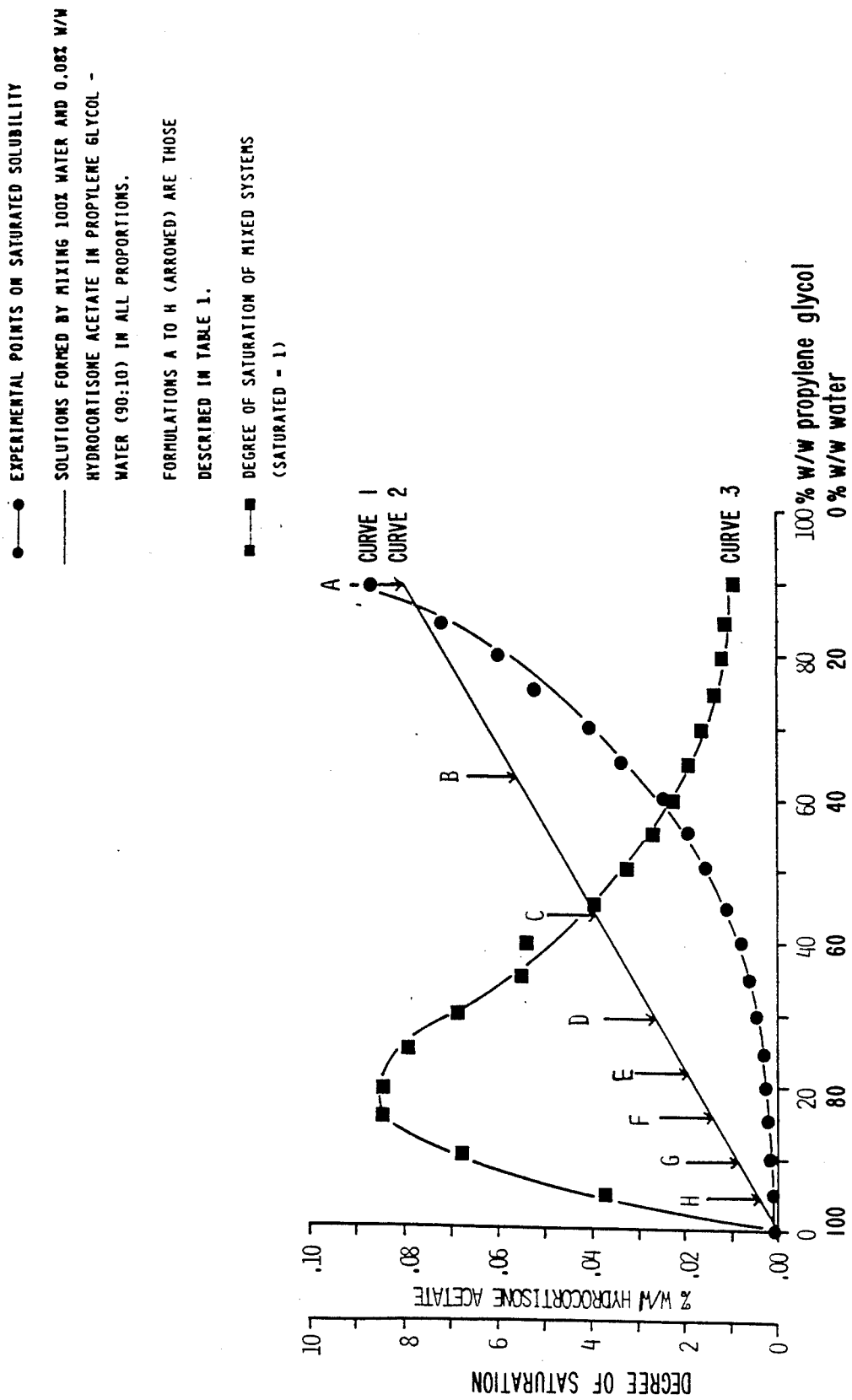

United States Patent [19]

Davis

[11] Patent Number: 4,940,701
[45] Date of Patent: * Jul. 10, 1990

[54] TOPICAL DRUG RELEASE SYSTEM

[75] Inventor: Adrian F. Davis, Weybridge, England

[73] Assignee: Beecham Group p.l.c., England

[*] Notice: The portion of the term of this patent subsequent to Aug. 30, 2005 has been disclaimed.

[21] Appl. No.: 131,015

[22] Filed: Dec. 10, 1987

Related U.S. Application Data

[63] Continuation-in-part of Ser. No. 693,770, Jan. 23, 1985, Pat. No. 4,767,751.

[30] Foreign Application Priority Data

Jan. 25, 1984 [GB] United Kingdom ............... 8401965
Dec. 11, 1986 [GB] United Kingdom ............... 8629639

[51] Int. Cl.$^5$ ............................................. A61K 31/56
[52] U.S. Cl. ...................................... 514/179; 514/937
[58] Field of Search ................................. 514/179, 937

[56] References Cited

U.S. PATENT DOCUMENTS

| | | | |
|---|---|---|---|
| 3,911,137 | 7/1975 | Miki et al. | 514/567 |
| 3,953,591 | 4/1976 | Snyder | 424/80 |
| 4,140,656 | 2/1979 | Mast | 252/545 |
| 4,244,942 | 1/1981 | Kamishita et al. | 424/81 |
| 4,602,040 | 7/1986 | Belsoce | 514/567 |
| 4,695,464 | 9/1987 | Alderman | 424/449 |
| 4,767,751 | 8/1988 | Davis | 514/179 |

FOREIGN PATENT DOCUMENTS

| | | |
|---|---|---|
| 151953 | 8/1985 | European Pat. Off. . |
| 193287 | 1/1986 | European Pat. Off. . |
| 213514 | 3/1987 | European Pat. Off. . |

*Primary Examiner*—Leonard Schenkman
*Attorney, Agent, or Firm*—Jacobs & Jacobs

[57] ABSTRACT

A pharmaceutical composition for topical administration consisting of two liquid phases designed to be admixed in situ or prior to use. The first phase contains a dissolved drug, and is preferably saturated in the drug, while the second phase is a chemically or physically different liquid from that in the first phase and contains no drug, but is miscible with the first phase. The two liquids are selected so that, on admixture of suitable volumes of the phases, the resultant drug concentration exceeds the saturated drug solubility in the resultant mixture. This produces a liquid mixture supersaturated in drug, which has been found to increase the rate of drug penetration into the skin. The two liquid phases may be gels, and the drug may be hydrocortisone.

At least one phase contains an antinucleant to improve stability of the resulting supersaturated solution.

10 Claims, 3 Drawing Sheets

TOPICAL DRUG RELEASE SYSTEM

This patent application is a continuation-in-part of my earlier filed U.S. patent application, Ser. No. 06/693,770 filed Jan. 23, 1985, now U.S. Pat. No. 4,767,751 the contents of which is incorporated herein by reference hereto.

The present invention relates to a composition and method, and in particular to a composition and method for topical application to and treatment of the human or animal body.

Hitherto, high levels of an active material (hereinafter referred to as 'the drug'), such as a pharmaceutically active material, have often been incorporated into a liquid carrier by forming a saturated solution of the drug in the carrier, thereby providing an effective topical treatment composition.

It has also been proposed (J. Pharm. Sci., 58, No. 9 (1969) pp 1098-1102; Coldman et al) to create a supersaturated solution of the drug from a subsaturated solution of the drug in a mixture of a volatile and a nonvolatile solvent. On topical application of the solution, the volatile solvent rapidly evaporates, thereby increasing the drug concentration to a supersaturated level. This has been found to increase the rate of drug penetration into the skin.

My earlier filed U.S. patent application, Ser. No. 06/693,770 filed Jan. 23, 1985, describes and claims a composition for topical application comprising a first liquid phase containing a drug (as herein defined) dissolved therein, and a second liquid phase, physically and/or chemically different from the first phase but miscible therewith, optionally containing the same drug (as herein defined) dissolved therein, the concentration of drug in each phase and the composition of the phases being such that, on admixture of the phases, the resultant total drug concentration is greater than the saturated drug solubility in the initially formed resultant mixture, thereby producing a mixture supersaturated with the drug. Such a composition enables improved drug penetration to be obtained by creating a supersaturated drug solution using a two-phase composition mixed in situ without the need for volatile solvent evaporation.

It has now been found that there can be a tendency for the drug to precipitate from the supersaturated solution obtained by the in situ mixing of the two phases of such a composition (because of the inherent tendency of a supersaturated solution to revert to the more stable saturated state). The tendency for such precipitation to occur will depend on a number of internal and external factors including, for example, the degree of supersaturation, the nature of the solute and solvent, the presence of extraneous material, and the ambient temperature.

It has now been found that the tendency for such precipitation to occur can be substantially reduced by the incorporation of an antinucleating agent in one of the two initial phases of the composition, with a consequent further improvement in the degree of drug penetration obtained.

Accordingly, the present invention provides a composition as defined above characterised in that at least one of the said first and second phases contains an antinucleating agent.

The present invention also has the further advantage of enabling still higher degrees of supersaturation of the drug to be obtained than were practically possible with the previously described compositions, which can also lead to an increase in the degree of drug penetration achieved.

The term 'liquid' as used herein includes viscous materials such as creams, ointments or gels.

The term 'drug' as used herein includes not only pharmaceutically active substances, but also, for example, other substances having a therapeutic or other beneficial effect and also cosmetic and like substances.

The antinucleating agent used in the compositions according to the invention may be present in either or both of the said first and second phases of the composition. Advantageously, it is present in at least the second phase, and it may additionally be present in the first phase. In any event, when the two phases are mixed in situ to provide the super-saturated solution, the antinucleating agent will, of course, be present in the resulting solution.

The antinucleating agent is suitably present in an amount of up to 2.0%, advantageously from 0.01 to 1.0% by weight, preferably from 0.1 to 0.5% by weight, of the antinucleating agent, based on the total weight of the composition.

The antinucleating agent should be soluble in the phase or phases in which it is present and, of course, in the resulting mixed solution.

Examples of suitable antinucleating agents are hydroxyalkylcelluloses, such as hydroxypropylmethylcellulose and hydroxypropylcellulose, polyvinylpyrrolidone and polyacrylic acid. A mixture of two or more different antinucleating agents may be used. In the event that an antinucleating agent is included in each of the first and second phases of the composition, the same or different antinucleating agents may be included in each phase.

The choice of a suitable anti-nucleating agent will depend both on the particular drug and the particular carrier system being used, but suitable anti-nucleating agents can readily be chosen by simple experiment. This may be done, for example, by preparing samples of the desired final supersaturated drug solution; adding a selection of anti-nucleating agents (in, say, 1% concentration), one to each sample; allowing the samples to stand for, say, 2 hours; and noting which solutions have remained clear, and thus stable. If desired, following such initial screening, further standard analytical techniques may be used to quantify the effects of selected anti-nucleating agents.

In the composition according to the invention, the relative proportions by volume of the first liquid phase to the second liquid phase is advantageously from 1:1 to 1:9, preferably from 1:1 to 1:3.

The second phase need not contain any drug, provided the resultant mixture is supersaturated in drug.

Each phase may contain one or more drugs, in amounts such that the resultant mixture is supersaturated in one or more drugs.

Preferably, the first phase comprises a suitable solubiliser, optionally in admixture with a pharmaceutically acceptable carrier, and the second phase comprises a pharmaceutically acceptable carrier, optionally in admixture with a suitable solubiliser.

Preferably the first phase comprises from 0 to 50% of the carrier and from 50 to 100% of the solubiliser, and the second phase comprises from 0 to 50% of the solubiliser and from 50 to 100% of the carrier.

Examples of suitable solubilisers include propylene glycol, 1,3-propylene diol, polyethylene glycol, ethanol, propanol, glycerine, dimethyl sulphoxide, dimethyl acetamide, dimethyl formamide, hexylene glycol, propylene carbonate, higher alcohols, higher carboxylic acids, fatty esters, mineral and vegetable oils, and mixtures of any two or more thereof. Examples of suitable higher alcohols and carboxylic acids include those having from 12 to 18 carbon atoms, for example lauryl and stearyl derivatives. Examples of suitable fatty esters include isopropylmyristate and glyceryl mono-esters. Examples of suitable mineral and vegetable oils include liquid paraffin, castor oil, soyabean oil and olive oil.

In the case of ionisable drugs, aqueous acid or alkali buffers are also useful as solubilisers.

The carrier is suitably a liquid which is miscible with the solubiliser but which has a different lipophilicity. A preferred carrier (when the solubiliser is not a higher alcohol or carboxylic acid, a fatty ester, or a mineral or vegetable oil) comprises water. When the solubiliser is a higher alcohol, a higher carboxylic acid, a fatty ester, or a mineral or vegetable oil, the carrier is preferably a lower alcohol or polyol, for example propylene glycol, 1,3-propylene diol, polyethylene glycol, ethanol, or propanol.

Preferably, the first phase comprises a mixture of carrier and solubiliser, and the second phase comprises the same carrier, optionally admixed with the same solubiliser in a different weight ratio from the carrier:-solubiliser weight ratio of the first phase.

It has been found advantageous to formulate the composition so that the drug is initially saturated in the first phase but is absent from the second phase. The degree of supersaturation, and hence rate of drug release, of the final mixture can then easily be predicted from the saturated drug solubility curve for the particular solubiliser/carrier system.

The degree of improvement in drug penetration rate in situ will depend largely on the ratio of supersaturated drug concentration to saturated drug concentration. A ratio of greater than 1:1 is considered useful and ratios of from 2:1, for relatively slow penetration, to 10:1, for rapid penetration, are preferred. By means of the present invention, extremely high degrees of supersaturation can be obtained, and ratios of 50:1 or greater are achievable. Due to the inefficiency of percutaneous absorption, such highly supersaturated systems are of great benefit.

Each phase may be thickened with a suitable thickening or gelling agent of either natural or synthetic origin. Examples of thickening and gelling agents are natural gums, tragacanth, carrageen, pectin, agar, alginic acid, cellulose ethers and esters, xanthan gum, guar and locust bean gum, bentonite (a colloidal hydrated aluminium silicate), veegum (colloidal magnesium aluminium silicate), laponite (a synthetic hectorite), polyvinyl alcohol, Aerosil (a trademark, colloidal silica), and Carbopol (a trademark).

The composition of the invention may be packaged into a twin compartment pack ready for topical application by the user or patient. The user or patient would normally apply the two phases simultaneously to the treatment area, and then mix the phases together in situ to create the supersaturated drug system.

The two phases may also be mixed in the pack by breaking a membrane or seal separating the phases, and can then be dispensed from the pack as a supersaturated drug system. Suitable packs for such purposes are commercially available and examples thereof are (i) the dual tube 'Tube-in a Tube' (manufactured by Metal Box); (ii) the 'Panmix' twin compartment pack (manufactured by Panpack Limited) ('Panmix' is a trade mark); and (iii) the 'Instamix' twin compartment sachet (manufactured by Crest Packaging Limited).

A further possible arrangement is for the two phases to be packed into a single compartment, according to the method described in UK Patent Specification No. 962,757. In this case, the two phases must have sufficiently high viscosity to emerge from the compartment as a single extruded mass, and the phases should of course be stable at their interface when stored inside the compartment.

The composition of the invention is suitable for any medical, cosmetic or other treatment of the body surface, including the skin, scalp, nails and oral mucosa.

It is also envisaged that the composition will be of value in treating systemic diseases by the so-called transdermal route, in which a drug is applied topically for absorption through the skin for systemic treatment. At present, only well absorbed or very low-dose drugs have been found useful in transdermal systems. The composition of the present invention provides a means by which many drugs, which are not particularly well absorbed topically or which need to be delivered in high doses, can be administered effectively in a transdermal system. The phases can be mixed within a transdermal device such as the 'Transiderm-Nitro' (a trade mark) immediately before application to the skin.

Accordingly, in a further aspect the invention provides a transdermal device containing a composition according to the invention.

Suitable drugs for use in the composition and method of the invention are many and varied, and include the following types, with specific examples of each in brackets:

steriod (hydrocortisone); anti-bacterial (tetracycline); anti-septic (chlorhexidine); anti-fungal (econazole); anti-psoriasis (dithranol); anti-acne (retinoic acid); anti-dandruff (zinc omadine); treatment of head-lice (acaricide); anti-histamine (mepyramine); local anaesthetic (benzocaine or lignocaine); analgesic, anti-inflammatory (ibuprofen); and anti-plaque (triclosan).

Examples of drugs suitable for use in a transdermal device include beta-adrenoceptor blockers (propanolol), broncho-spasm relaxants (theopylline), anti-angina (glyceryl trinitrate), anti-travel sickness drugs (scopolamine), anti-histamines (chlorpheniramine), decongestants (phenylpropanolamine), anti-tussives (pholcodine), analgesics (codeine, flurbiprofen), and anti-coagulants (warfarin).

Figure 2:
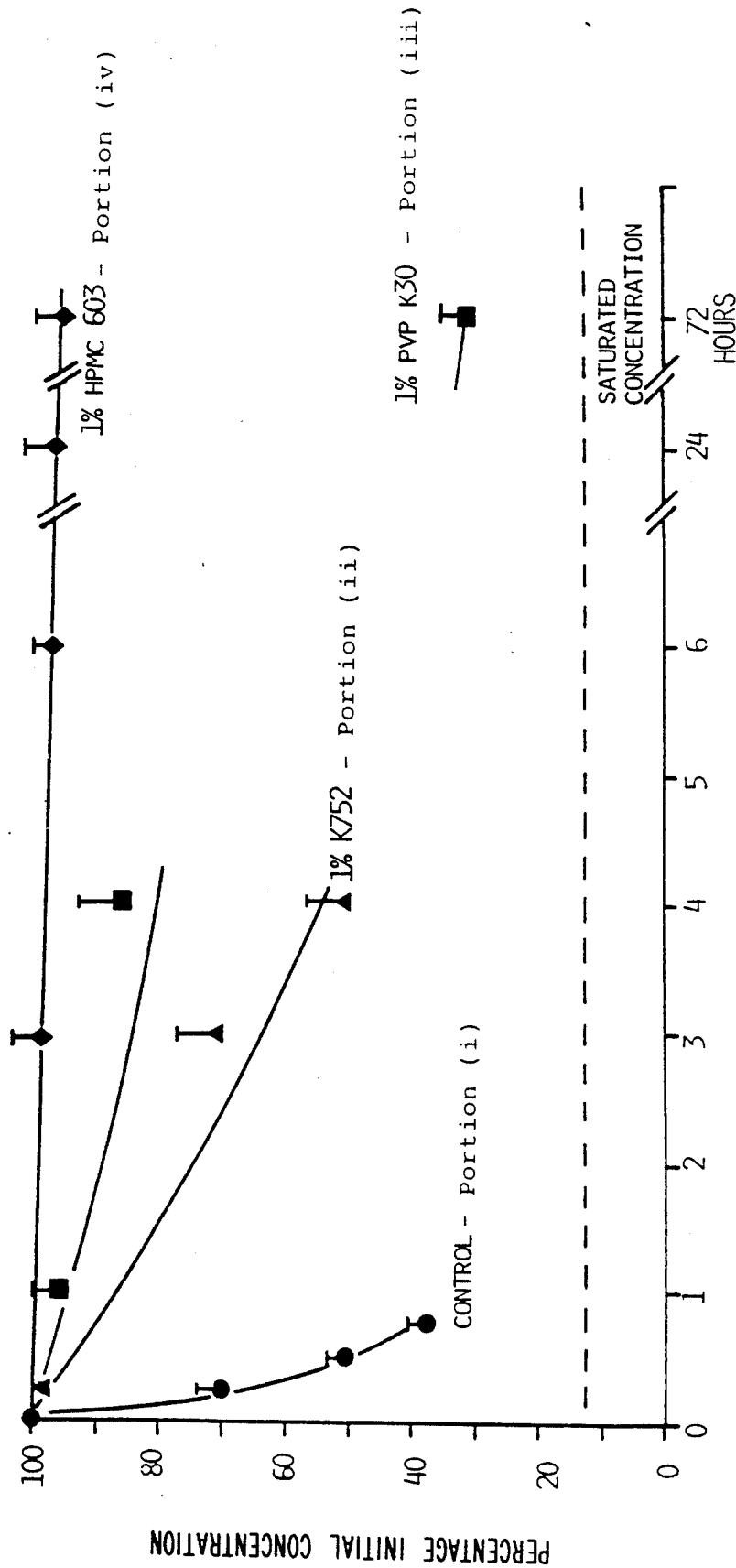
Figure 4:
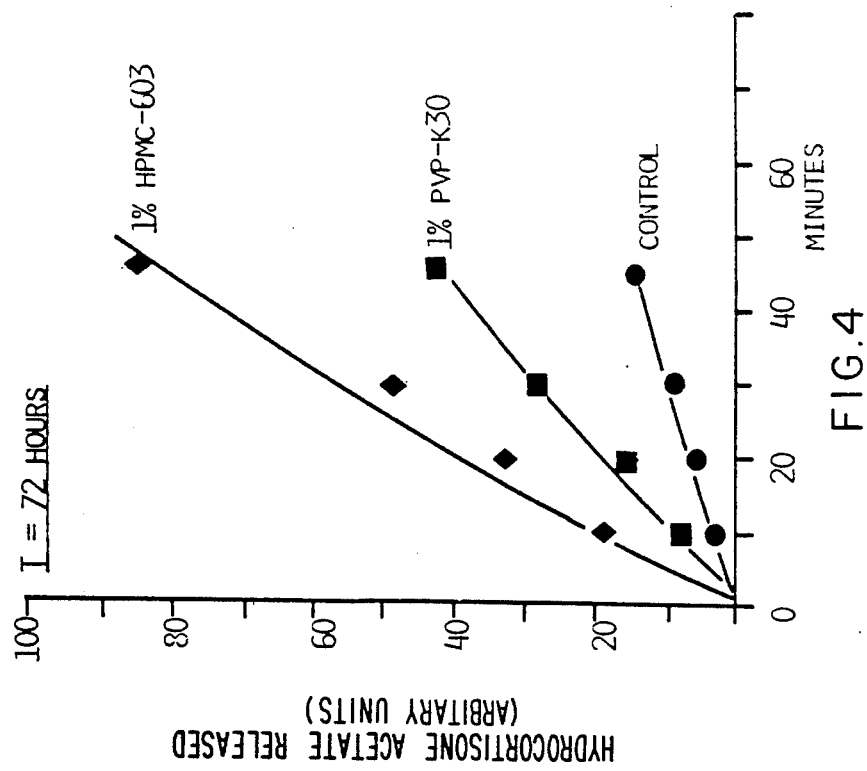
Figure 3:
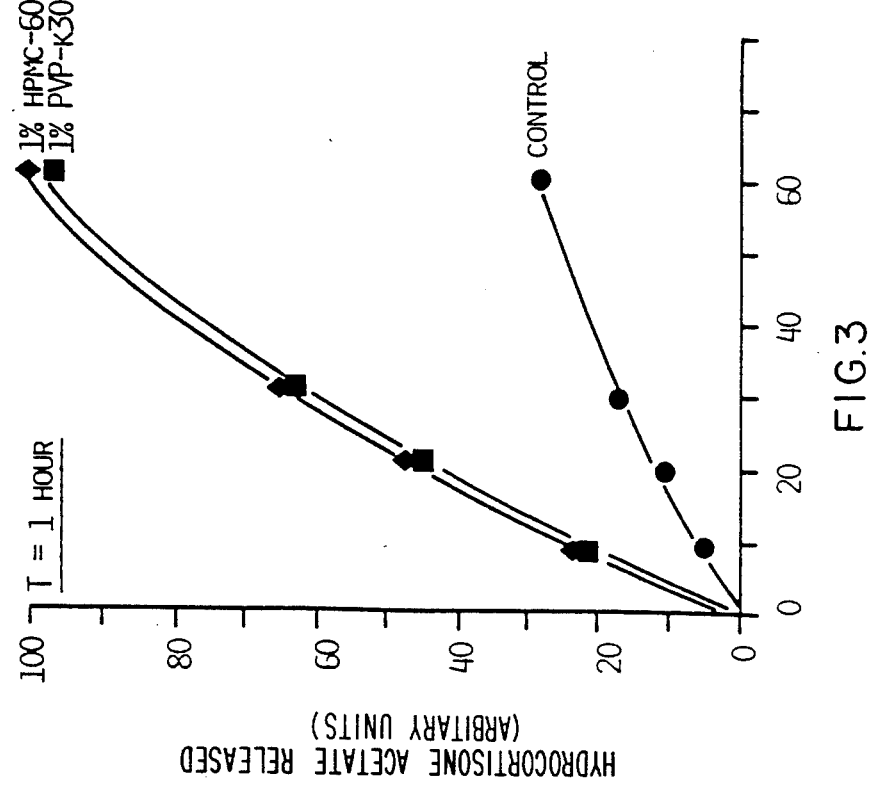

The following examples illustrate the invention with reference to the accompanying FIGS. 1 to 4, in which:

FIG. 1 is a graph showing solubility data of hydrocortisone acetate in water/propylene glycol mixtures, as more fully described in Example 1;

FIG. 2 is a graph showing the effect of various antinucleants on the precipitation of hydrocortisone acetate from supersaturated solutions in water/propylene glycol mixtures, as more fully described in Example 2; and FIGS. 3 and 4 are graphs showing the effect of various antinucleants on the in-vitro release of hydrocortisone acetate from supersaturated solutions in water/proplene glycol mixtures, as more fully described in Example 3.

EXAMPLE 1

Formation of supersaturated solutions

The saturation solubility of hydrocortisone acetate in mixtures of water and propylene glycol (varying from 100% water, through 50% water 50% propylene glycol, to 100% propylene glycol, in 5% steps (all percentages being weight/weight)) was determined and plotted to give the curve shown by round dots (Curve 1) in FIG. 1.

A solution of 0.08% hydrocortisone acetate in a mixture of 90% propylene glycol and 10% water was prepared (Formulation A) as the first phase. This was then mixed with various proportions of water plus antinucleant, as the second phase, as indicated in Table 1 below, to give supersaturated Formulations B to H as plotted on the straight line (Curve 2) in FIG. 1. The resulting supersaturated concentration of hydrocortisone acetate in the diluted propylene glycol/water mixture is shown by Curve 2 and is given in Table 1.

The degree of supersaturation is determined by dividing the points on Curve 2 (at 5% intervals) with the corresponding saturation solubility on Curve 1 for the same water/propylene glycol mixture, to give Curve 3 (square dots) in which the Degree of Saturation obtained by diluting Formulation A is plotted against the resulting propylene glycol/water proportions.

It can be seen that, for a given initial drug composition (such as Formulation A), the addition of increasing amounts of water first increases the degree of saturation (Formulations B to D) until a plateau region is reached (Formulation E and F), whereafter the degree of saturation decreases again (Formulations G and H).

The compositions of the two phases in the composition according to the present invention are advantageously so chosen that, on being mixed together they give a super-saturated composition in the peak plateau region of the saturation curve, in order to achieve maximum supersaturation and thus maximum drug penetration.

TABLE 1

| FORMULATION | PARTS OF EACH SOLUTION MIXED | | RESULTANT CONCENTRATION % w/w | RESULTANT DEGREE OF SATURATION (SATURATED = 1) |
|---|---|---|---|---|
| | HYDROCORTISONE ACETATE 0.08% w/w IN 90:10 PROPYLENE GLYCOL:WATER (first phase) | WATER PLUS ANTINUCLEANT (second phase) | | |
| A | 1 | 0 | 0.080 | 0.9 |
| B | 2 | 1 | 0.053 | 2.0 |
| C | 1 | 1 | 0.040 | 4.0 |
| D | 1 | 2 | 0.027 | 6.8 |
| E | 1 | 3 | 0.020 | 8.0 |
| F | 1 | 4.3 | 0.015 | 8.4 |
| G | 1 | 7 | 0.010 | 7.0 |
| H | 1 | 15 | 0.005 | 4.0 |

EXAMPLE 2

Addition of antinucleating agents

A sample of supersaturated Formulation E (without antinucleant) was prepared by diluting Formulation A with three volumes of water as described in Example 1, and it was divided into four portions to which different antinucleating agents were added as follows:
  (i) none - control sample;
  (ii) 1% w/w polyacrylic acid K752 (from Goodrich Chemicals);
  (iii) 1% w/w polyvinylpyrollidone K30 (from BASF);
  (iv) 1% w/w hydroxypropylmethylcellulose 603 (from Shin-Etsu Chemical Co., Toyko).

The four portions were each left to stand at room temperature for up to 72 hours, during which time some of them tended to turn cloudy as hydrocortisone acetate tended to precipitate out from the supersaturated solution. Each portion was sampled periodically (at the respective time intervals shown by the points plotted in FIG. 2) and analysed by hplc to determine the content of hydrocortisone acetate remaining in solution (as a percentage of the initial 8-fold supersaturated concentration). The results are plotted in FIG. 2, which also shows (by dashed line) the saturated concentration for comparison.

It can be seen from FIG. 2 that the control sample (without antinucleant) was relatively unstable and the degree of supersaturation decreased fairly rapidly. In contrast thereto, all of Portions (ii) to (iv) had substantially improved stability, and in Portion (iv) practically no precipitation had occurred even after 72 hours.

EXAMPLE 3

In-vitro release from supersaturated solutions

Three 20 ml portions of Formulation E, respectively containing no antinucleant (control) and containing antinucleants as given at (iii) and (iv) in Example 2, were left to stand for 1 hour. 20 ml of isopropylmyristate was then added to each portion and the portions were agitated for a further hour. The isopropylmyristate phase of each portion was sampled after 10, 20, 30 and 60 minutes, and analysed by hplc to determine its hydrocortisone acetate content.

The procedure was repeated with the variations that the portions were first left to stand for 72 hours before addition of the isopropylmyristate, and that sampling was effected at 10, 20, 30 and 45 minutes.

The hydrocortisone acetate content of the isopropylmyristate serves to indicate the amount of hydrocortisone acetate released from the supersaturated solution, which will be a function of the degree of supersaturation.

The results are plotted in the two graphs given in FIG. 3. It can be seen that, in all cases, the portions containing antinucleants gave substantially improved release of hydrocortisone acetate as compared with the control portions. This shows that those portions had retained a higher degree of supersaturation than had the control portions, as a result of improved stability by the presence of the antinucleant.

These results also confirm that the improved stability shown in Example 2 is a true improved supersaturation stability, rather than an apparent improved stability obtained by actually increasing the saturation solubility of the system. In the latter case, the actual degree of supersaturation would in fact have been decreased and the solutions would therefore not show improved release of the hydrocortisone acetate.

EXAMPLES 4–8

Formation of gelled supersaturated solutions

Gelled supersaturated solutions, analogous to the liquid supersaturated solutions described in Examples 1 and 2, are prepared by formulating two separate phases (analogous to the first and second phases in Table 1 above) with a gelling agent incorporated in at least one of the two phases and an antinucleating agent incorporated in at least one of the two phases. On mixing of the two phases, gelled supersaturated solutions are formed as described above with reference to FIG. 1.

Examples 4–8 below give examples of suitable two-phase formulations for the preparation of such gelled supersaturated solutions. In each of those formulations, the gelled supersaturated solution may be formed by mixing one part of the first phase with three parts of the second phase. A suitable dye is for example Brilliant Blue FCF. Suitable preservatives are for example Kathon CG, Euxyl K100 (a mixture of isothiazolinones and benzyl alcohol), Hiquest 20 (disodium etidronate), and disodium edetate.

EXAMPLE 4

| First phase | % w/w |
| --- | --- |
| hydrocortisone acetate | 0.08 |
| propylene glycol | 90.00 |
| dye | 0.01 |
| deionised water | 9.91 |
| | 100.00 |
| Second phase | |
| carbopol 934 | 1.00 |
| triethanolamine | 1.25 |
| polyacrylic acid | 1.00 |
| preservative | 0.25 |
| deionised water | 96.50 |
| | 100.00 |

EXAMPLE 5

| First phase | % w/w |
| --- | --- |
| hydrocortisone acetate | 0.08 |
| propylene glycol | 90.00 |
| polyvinylpyrrolidone | 0.50 |
| dye | 0.01 |
| deionised water | 9.41 |
| | 100.00 |
| Second phase | |
| Silica (Aerosil) | 1.50 |
| hydroxypropylcellulose | 0.50 |
| preservative | 0.15 |
| deionised water | 97.85 |
| | 100.00 |

EXAMPLE 6

| First phase | % w/w |
| --- | --- |
| hydrocortisone acetate | 0.08 |
| propylene glycol | 89.47 |

EXAMPLE 6-continued

| | % w/w |
| --- | --- |
| polyvinylpyrrolidone | 0.50 |
| dye | 0.01 |
| deionised water | 9.94 |
| | 100.00 |
| Second phase | |
| carbopol 940 | 0.70 |
| sodium hydroxide | 0.28 |
| hydroxypropylmethylcellulose | 0.50 |
| preservative | 0.23 |
| deionised water | 98.29 |
| | 100.00 |

EXAMPLE 7

| First phase | % w/w |
| --- | --- |
| hydrocortisone acetate | 0.08 |
| propylene glycol | 90.00 |
| polyvinylpyrrolidone | 0.50 |
| dye | 0.01 |
| deionised water | 9.41 |
| | 100.00 |
| Second phase | |
| xanthan gum | 0.50 |
| polyacrylic acid | 0.50 |
| preservative | 0.15 |
| deionised water | 98.85 |
| | 100.00 |

EXAMPLE 8

| First phase | % w/w |
| --- | --- |
| hydrocortisone acetate | 0.08 |
| propylene glycol | 90.00 |
| polyacrylic acid | 0.50 |
| dye | 0.01 |
| deionised water | 9.41 |
| | 100.00 |
| Second phase | |
| carbopol 940 | 1.00 |
| triethanolamine | 1.25 |
| hydroxypropylcellulose | 0.50 |
| preservative | 0.15 |
| deionised water | 97.10 |
| | 100.00 |

What is claimed:

1. In a pharmaceutical composition for topical application, comprising a first liquid phase and a second liquid phase different from the first phase but miscible with the first phase upon admixture therewith, at least one of said phases comprising a drug dissolved therein, the concentration of said drug in each phase in which said drug is present and the composition of the phases being such that, on admixture of the phases, the total drug concentration in the initially formed resultant mixture is greater than the saturated drug solubility in said initially formed resultant mixture, whereby said resultant mixture is supersaturated with the drug, the improvement wherein at least one of said first and second phases comprises from 0.01 to 2% by weight, based on the total weight of the composition, of an antinucleating agent.

2. A composition as claimed in claim 1, further comprising a solubiliser and a pharmaceutically acceptable carrier, said first phase comprising from 0 to 50% of said carrier and from 50 to 100% of said solubiliser and said second phase comprising from 0 to 50% of said solubiliser and from 50 to 100% of said carrier.

3. A composition as claimed in claim 1, wherein the antinucleating agent is present in a total amount of from 0.1 to 0.5% by weight, based on the total weight of the composition.

4. A composition as claimed in claim 1, wherein the antinucleating agent is hydroxyalkylcellulose, polyvinylpyrrolidone, and polyacrylic acid.

5. A composition as claimed in claim 1, wherein an antinucleating agent is present in each phase of the composition.

6. A composition as claimed in claim 2, wherein the solubiliser is propylene glycol, 1,3-propylene diol, polyethylene glycol, ethanol, propanol, glycerine, dimethyl sulphoxide, dimethyl acetamide, dimethyl formamide, hexylene glycol, propylene carbonate, higher alcohols, higher carboxylic acids, fatty esters, mineral and vegetable oils, or mixtures of any two or more thereof.

7. A composition as claimed in claim 1, wherein the drug is initially saturated in the first phase and is absent from the second phase.

8. A twin compartment pack containing a composition according to claim 1, the first liquid phase being in one compartment and the second liquid phase being in the other compartment.

9. A transdermal device containing a composition according to claim 1.

10. A method for topical treatment of the human or animal body which comprises applying thereto a pharmaceutical composition according to claim 1.

* * * * *